United States Patent [19]

Kataoka et al.

[11] Patent Number: 4,482,320

[45] Date of Patent: Nov. 13, 1984

[54] FACE BOW OF THE MANDIBULAR MOTION DIAGNOSTIC DEVICE

[75] Inventors: Kenzo Kataoka, Otsu; Minoru Imazato, Uji, both of Japan

[73] Assignee: Kabushiki Kaisha Morita Seisakusho, Kyoto, Japan

[21] Appl. No.: 484,149

[22] Filed: Apr. 12, 1983

[30] Foreign Application Priority Data

Apr. 20, 1982 [JP] Japan ............................. 57-58223[U]

[51] Int. Cl.³ .......................................... A61C 19/04
[52] U.S. Cl. .................................................... 433/69
[58] Field of Search .................. 128/777; 433/69, 27, 433/55, 68, 73

[56] References Cited

U.S. PATENT DOCUMENTS

| | | | |
|---|---|---|---|
| 2,119,823 | 6/1938 | Miller et al. | 433/68 |
| 3,074,166 | 1/1963 | Skallerup | 433/69 |
| 4,034,474 | 7/1977 | Lee | 433/69 |
| 4,234,306 | 11/1980 | Hamada et al. | 433/55 |
| 4,354,836 | 10/1982 | Santoni | 433/73 |

FOREIGN PATENT DOCUMENTS

232447  4/1967  U.S.S.R. .............................. 128/777

Primary Examiner—John J. Wilson
Attorney, Agent, or Firm—Koda and Androlia

[57] ABSTRACT

This invention relates to a face bow for a mandibular motion diagnostic device and more particularly to a face bow as a component of a device for measuring a patient's mandibular motion and reproducing it precisely by the use of a mandibular model on the basis of the measured data. The face bow is attached in a fixed positional relationship to the patient's mandible as measurement is taken of the motion thereof and is shifted onto the mandibular model upon completion of the measurement so that the patient's dental arch in its actual position is precisely reproduced in the mandibular model.

2 Claims, 8 Drawing Figures

FACE BOW OF THE MANDIBULAR MOTION DIAGNOSTIC DEVICE

BACKGROUND OF THE INVENTION

1. Field of the Invention

The present invention relates to what is called a face bow of a mandibular motion diagnostic device, more particularly to a face bow as a component of a device for measuring a patient's mandibular motion and reproducing it precisely by the use of a mandibular model on the basis of the measured data, which is attached in a fixed positional relationship to the patient's mandible as measurement is taken of the motion thereof and is shifted onto the mandibular model upon completion of the measurement so that the patient's dental arch in its actual position is precisely reproduced in the mandibular model.

2. Prior Art

In view of the significance of the mandibular motion in dental analyses, various methods and devices for measuring the mandibular motion have been proposed. They are, however, invariably mere measuring devices, having nothing to do with reproduction of the mandibular motion.

The present inventor has, therefore, further developed the idea to supply the information obtained about the mandibular motion by such a measuring device to a reproducing device so as to have the patient's mandibular motion precisely reproduced thereby, and which could thus provide a far more realistic diagnostic device than its earlier counterparts which are good soley for measuring.

This diagnostic device is based on the idea of imaginarily setting an isosceles triangle with the center of the anterior section of the mandible as the vertex and the posterior ends of the lateral sections thereof as the base points, assuming the plane defined by this isosceles triangle as a rigid plane representing the mandible, and grasping the mandibular motion as three-dimensional motion of this plane. In particular, this invention consists of setting the points to be measured (measuring points) at points which correspond to the above-mentioned three points each consisting of a spot light sources, measuring the amount of displacement of the individual measuring points and converting the measured amount of displacement in the computing unit into corresponding two-dimensional coordinate data to be stored as position information in the memory unit.

Meanwhile, in the reproducing unit three reference points for reproduction are set where their positional relationships to the mandibular model are equal to those between the above-mentioned measuring points and the patient's mandible. These reference points for reproduction are connected with respective drive units and the position information read out of the memory unit is inputted to the individual drive units so that the plane representing the mandible defined by the three reference points for reproduction is caused to move with the reference points for reproduction as datum points for motion; and as a result, the mandibular model is caused to precisely reproduce the three-dimensional motion of the patient's mandible. Details thereof are disclosed in the specification of an earlier application filed in the name of the present applicant (Japanese patent application No. Sho-57-57721) which is incorporated herein by reference and hence description of any further details is omitted here. In this diagnostic device, however, one thing remains unsolved; that is, the problem of how to locate precisely the patient's dental arch in the mandibular model in the process of reproducing the structure of the patient's mandible. Even if the motion of the whole mandible except for the dental arch could be precisely reproduced, failure to reproduce the position of the critical dental arch in the mandibular model is bound to make such information imperfect for diagnostic purpose. Hitherto there was known a means of actually measuring the position of the dental arch in the patient's mandible and shifting it onto an articulator, the means having nothing to do with such a reproducing device. This means includes a reference bar called "face bow" linking the patient's auricular holes with the bottoms of his orbits and a dish-retaining bar having fixedly attached to it a dental dish filled with an impression material for taking the impression of the dental arch. These are connected together and the face bow is further connected as it is used with a separate head fastening member freely adjustable in length, freely rotatable and tiltable. The above-mentioned face bow is set on the patient's head and the dental dish in the patient's mouth cavity. The head fastening member is then fastened to the face bow and the dental dish steadied with respected to each other and the patient is ordered to bite the impression material. The bitten impression material is then taken out, the face bow is released from the head and is shifted onto the articulator. The articulator has provided thereon a reference plane corresponding to the auricular holes and the bottom of the orbits; and when the occlusal impression on the dental dish is set thereon together with the face bow fixedly connected with the dental dish, the positional relationship between the articulator and gnathic model can be grasped. Such a conventional means, although it is somehow applicable to the above-mentioned reproducing system, can hardly have either the auricular holes or the bottom of orbits as accurate reference points therefor and errors of approximately 1 mm are inevitable. Accordingly, the high precision of motion in the reproducing system is bound to be affected thereby.

SUMMARY OF THE INVENTION

The present invention, which is intended to eliminate the drawbacks of the above-described prior art, relates to a face bow of a mandibular motion diagnostic device, which is to be fixedly set around a patient's mandible for measurement to be taken with respect to the above-described three reference points for measurement (spot light sources) set along the patient's mandible; and after the measurement, the measurements are shifted onto an articulator to be so set thereon that the reference points for measurement agree with the articulator's reference points for reproduction of the position of the patient's dental arch so that they are precisely reproduced on the mandibular model. The reference points for measurement are arranged to precisely agree with the reference points for reproduction; and since the reference points for reproduction are concretely located each at the center of motion of a spherical joint, the retaining member with the reference points for measurement set thereon is rotatable up to 90 degrees for setting of the reference points for measurement in the respective bearings to be facilitated thereby.

This an other objects and advantages and further description will now be discussed in connection with the drawings in which:

DETAILED DESCRIPTION OF THE INVENTION

Figure 1:
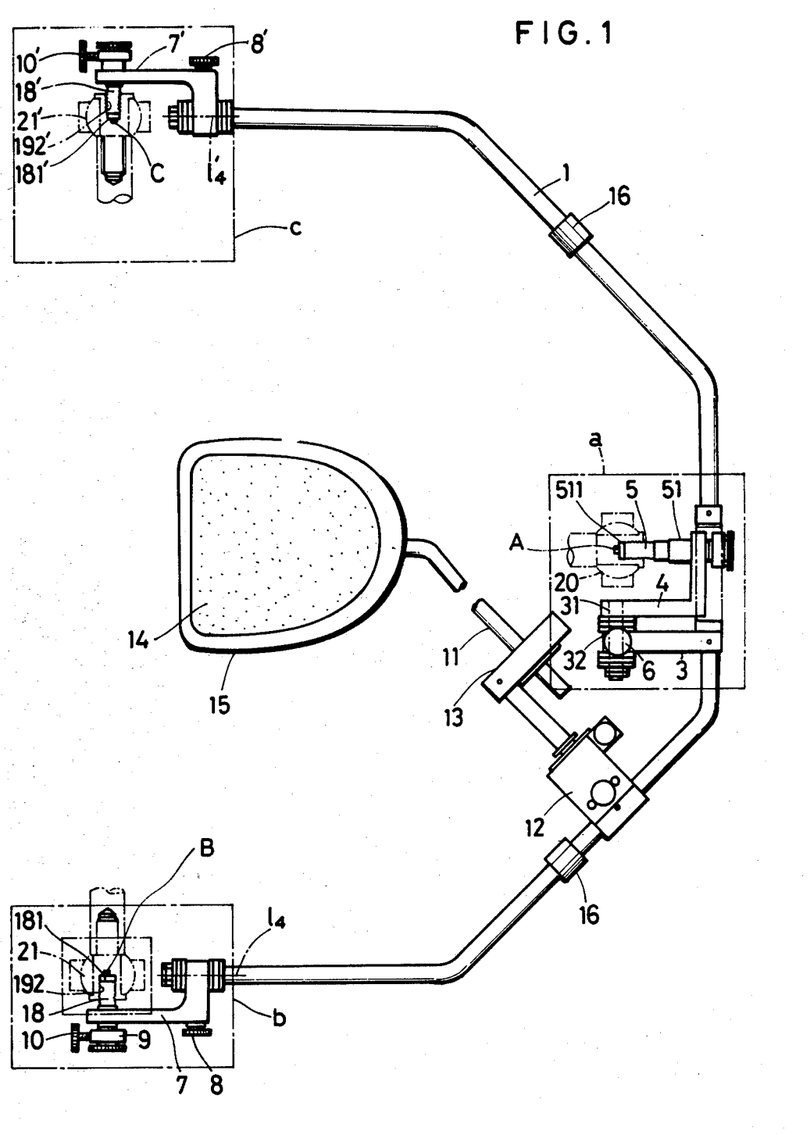
FIG. 1 is a plan view showing a preferred embodiment of a face bow of the present invention.
Figure 2:
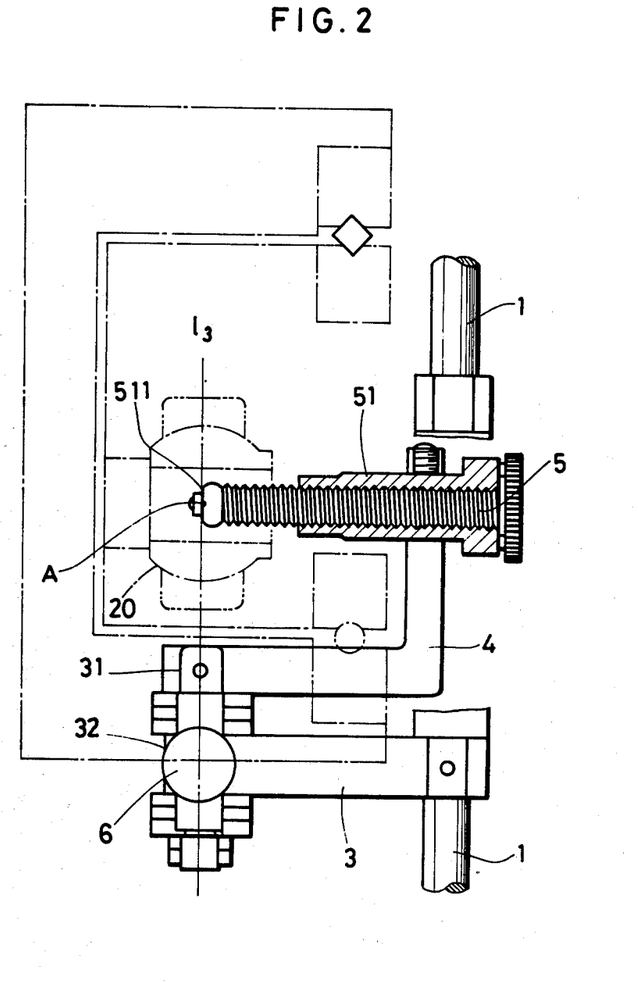
FIG. 2 is a partly sectioned enlarged view of a section "a" of the above-mentioned embodiment marked off by chain line.
Figure 3:
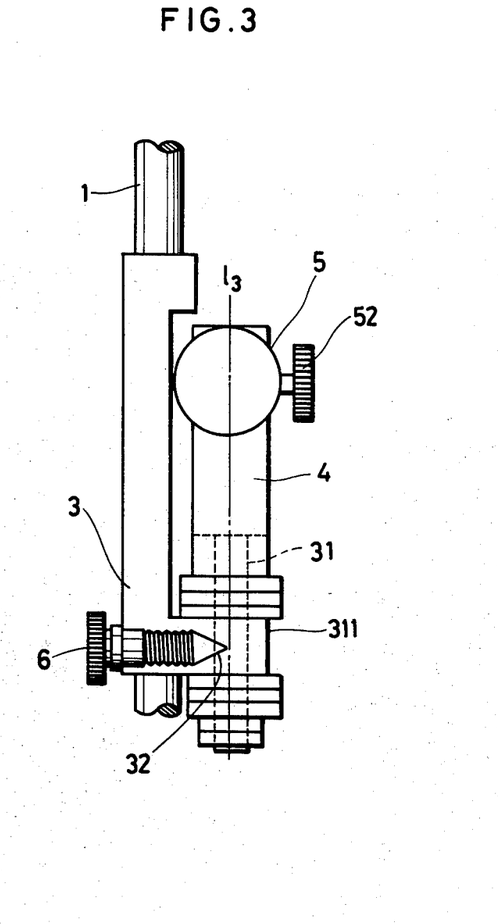
FIG. 3 is a front view thereof.
Figure 4:
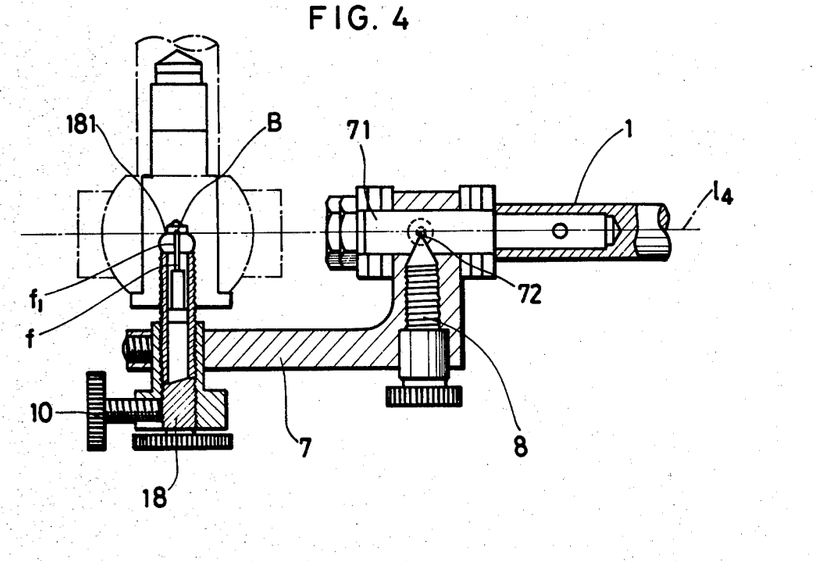
FIG. 4 is a partly sectioned enlarged view of a section "b" in FIG. 1.

Referring now to FIG. 1, numeral 1 designates a face bow to be set around a patient P's mandible (lower jaw) LJ so that its relative position with respect to the mandible (lower jaw) LJ is kept constant throughout the time of measurement. Three spot light sources A, B and C as reference points for measurement (namely reference points for reproduction) and are attached to the face bow 1 in fixed positional relationships therewith. These spot light sources A, B and C are, as mentioned above, for determining a rigid plane representing the patient's mandible (lower jaw) LJ, A being the center of the mandible's anterior section and B and C being symmetrical points in both lateral sections of the mandible, and the $\triangle ABC$ constitutes an isosceles triangle. The three spot light sources A, B and C are attached to the face bow 1 by the use of angle members 4, 7 and 7', and the way the spot light source A is attached is shown in detail in FIGS. 2 and 3 and that for the spot light source B [identical with C] is shown in FIG. 4 respectively. As shown in FIGS. 2 and 3, the spot light source A is attached by the use of two angle members 3 and 4 and a retaining screw 5. First the angle 3 is connected with the face bow 1 and a mounting shaft 31 is set through a through-hole 311 in the member 3, and one end of another angle 4 is connected to the mounting shaft 31. The other end of the angle 4 has set therethrough an inner-threaded sleeve nut 51. The sleeve nut 51 has engaged therein a retaining screw 5 of a small screw pitch to be freely displaceable forward and back, and a set screw 52 for this retaining screw 5 (FIG. 3) is set through the sleeve nut 51. The tip 511 of the retaining screw 5 coincides with the axis $l_3$ of the mounting shaft 31 and the spot light source A is fixedly retained thereby.

An example of the retaining mechanism for another spot light source B is shown in FIG. 4 in which the retaining screw 5 has a longitudinal through-hole for accommodating fibre $f_1$ therein. In this through-hole $f_1$ a photo-conductive fibre f is fixedly retained with its tip located on the axis $l_3$, and the same mechanism is adopted for the spot light source C, too. The mounting shaft 31 is made to be rotatable by 90° from the position shown in FIGS. 1 and 2 where the axis of the retaining screw 5 is in a horizontal plane with its tip pointing inward of the face bow 1 to the position where the axis of the shaft 51 is in a vertical plane with its tip pointing upward. There are provided at the corresponding positions in the periphery of the mounting shaft 31 small holes (or notches) 32 (see FIG. 3) 90° apart from each other so that the axis of the screw 31 can be fixed in either of the above-mentioned two alternative positions. A mating set screw 6 is set through a sleeve 311 with its tip in the small hole 32. In the case of the spot light source 7, a single angle 7 is directly attached to the end of the face bow 1 as shown in FIG. 1. As is apparent from the figure, the face bow has set therethrough a mounting shaft 71 coaxially and freely rotatably and one end of the angle 7 is connected with this mounting shaft 71. The mounting shaft 71, like its counterpart 31, is provided at its periphery with two small holes (or notches) 90° apart from each other and a set screw 8 set through the bent end portion of the angle 7 has its tip in this small hole 72 for checking rotation of the mounting shaft 71. This mounting shaft 71 is made to be freely rotatable by 90°. At the other end of the angle 7, a retaining screw 18 is set through a sleeve nut 9 to be freely movable forward and back, and there is provided a set screw 10 for fixing thereof. The tip 181 of this retaining screw 18 coincides with the axis $l_4$ of the above-described mounting shaft 71 and the spot light source B is provided thereon. The way the spot light source C is retained is the same as described above for the spot light source B. Hence detailed description about spot light source C is herein omitted in order to avoid redundancy. The corresponding parts and members are, however, indicated by like numerals distinguishing '.

The spot light sources A, B and C are all shown in FIG. 1 as emitting light inward of the face bow 1. In the measuring device (shown in FIG. 5), however, the spot light sources A, B and C are all arranged to emit light upward. Numeral 11 in FIG. 1 designates a dental dish retaining bar connected with the face bow 1 by two connecting members 12 and 13 which retains at its tip a dental dish 15 filled with an impression material 14 substantially level. Numeral 16 designates freely extensible and retractable joints, connected amid the face bow 1, which are used for properly modifying the size as well as shape of the face bow 1.

Figure 5:
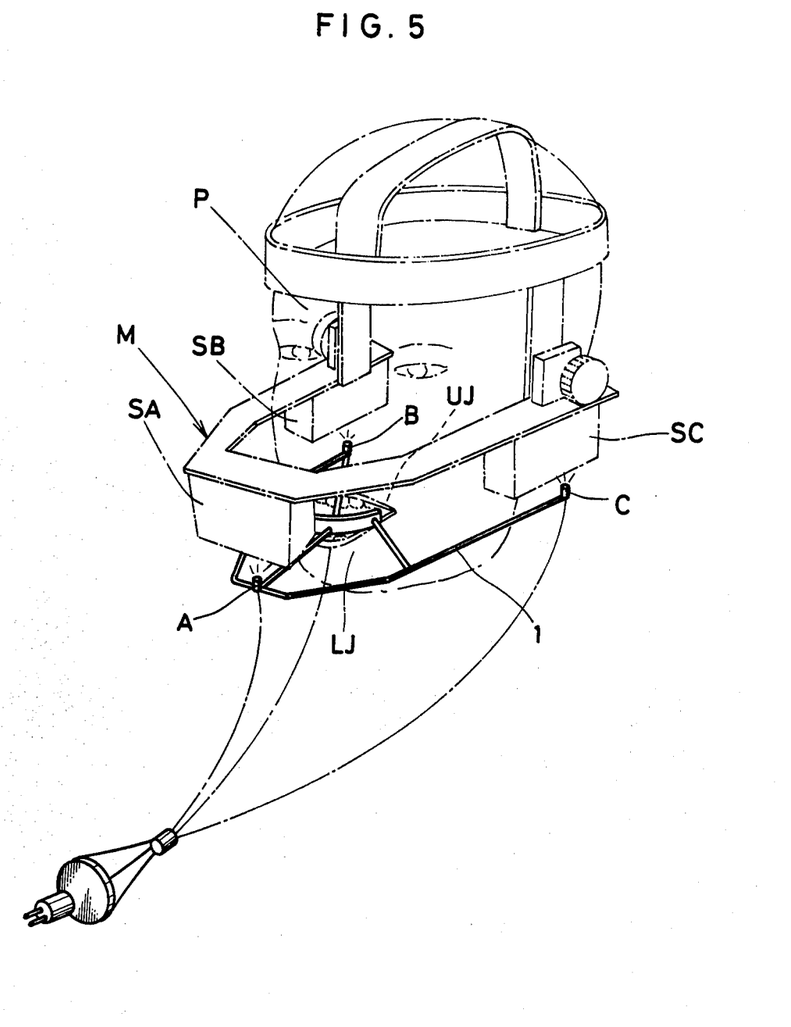
FIG. 5 is a schematic illustratory view of the measuring device of the present invention showing it in use.
Figure 6:
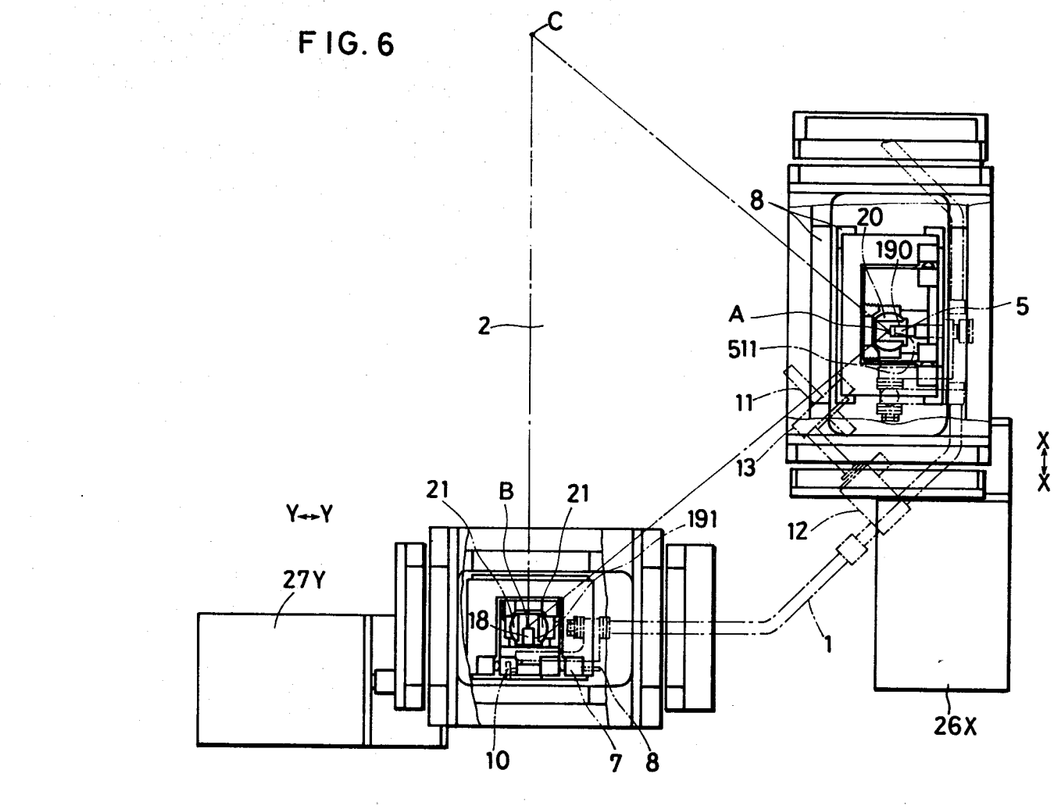
FIG. 6 is a partly cut-off plan view of a reproducing device of the present invention.

Now described is the way the face bow of the present invention is used. Referring to FIG. 5, the face bow 1 is so attached that the individual spot light sources A, B and C have their positional relationship with the patient's mandible (lower jaw) LJ kept constant and emit light right upward in the course of any gnathic motion. The dental dish 15 is then inserted into the patient P's mouth cavity. The way it is fixed with respect to the patient P has many alternatives, hence its illustration is here omitted. The spot light sources A, B and C so arranged serve as the reference points for measurement of gnathic motion with their relative positions with respect to the maxilla (upper jaw) UJ immovably fixed. Their motions are detected by corresponding sensors SA, SB and SC as amounts of displacement as a function of time, and the detected amount of displacement is then converted into the corresponding two-dimensional position coordinates in a computing unit (not shown) to be subsequently stored in a memory unit (not shown). With the memorizing of the coordinate data completed, the face bow is detached from the patient P and shifted onto a reproducing device 17. The procedure thereof is illustrated in FIGS. 6 and 7.

Figure 8:
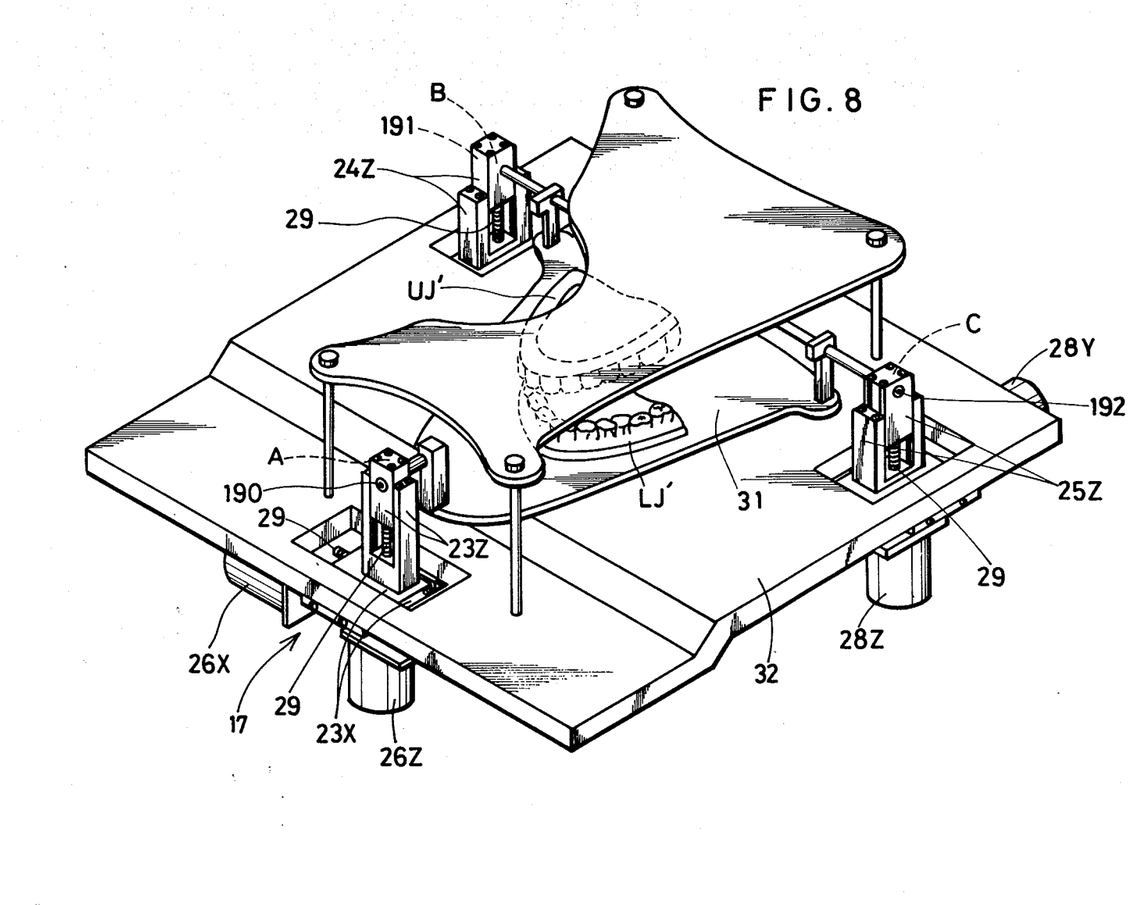
FIG. 8 is a schematic perspective view of the reproducing device.

As seen from FIG. 8, the reproducing device 17 includes a maxilla (upper jaw) model UJ' and a mandibular (lower jaw) model LJ', has freely rotatable and bendable spherical joints 20, 21 and 22 connected to a mandibular (lower jaw) model supporting plate 31 in fixed positional relationships therewith and the centers of motion of these joints 20, 21 and 22 serve as the reference points for reproduction. Thses joints 20, 21 and 22 have connected therewith slide mechanisms 23, 24 and 25 which are driven to slide in two of the orthogonal three dimensional directions and allowed to slide in the remaining one-dimensional direction. These slide mechanisms 23, 24 and 25 are connected with one pair each of pulse motors 26/26, 27/27 and 28/28 (with distinguishing suffixes to be described below). To these motors the corresponding pieces of two-dimensional position coordinate information are inputted from the above-described memory so that the plane defined by the joints 20, 21 and 22 and corresponding to the mandible (not shown) is caused to move through the respective slide mechanisms 23, 24 and 25 so as to allow a mandible supporting plate 31 to make three-dimensional motion precisely reproducing the patient P's mandibular motion.

Figure 7:
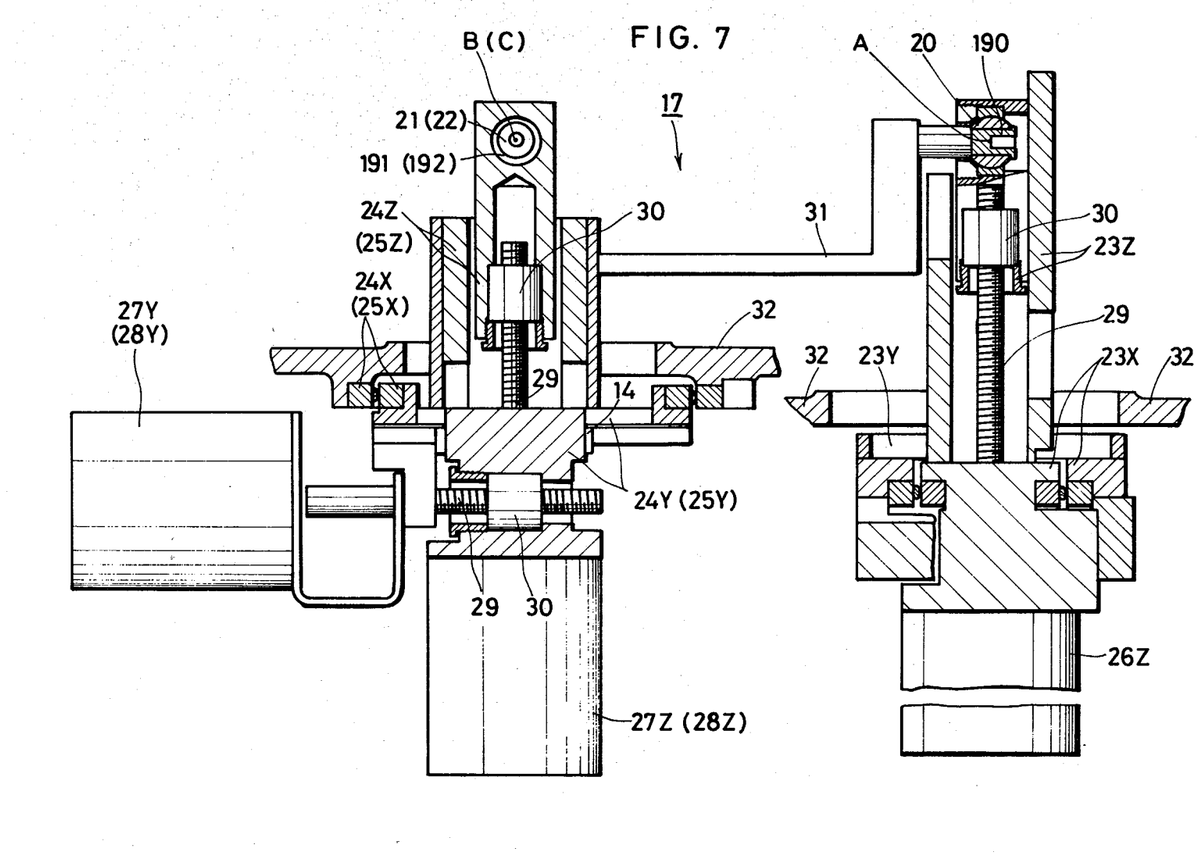
FIG. 7 is a partly sectioned side view of FIG. 6.

In FIG. 7 the respective slide mechanism 23, 24 and 25 are driven by the corresponding pairs of pulse motors 26 . . . in the vertical Z direction and lateral X direction with respect to the reference point for reproduction A [that is, the spherical joint 20]; and in the vertical Z direction and longitudinal Y direction with respect to the reference points for reproduction B and C. The joints are also allowed to slide in the remaining one direction following other joints being driven in the same sense and hence in the figure the identifying symbols (numerals) for the above-mentioned slide mechanisms and pulse motors are provided with distinguishing suffixes indicating the respective slide directions. The relationship between the slide mechanisms and pulse motors for (or with respect to) the reference point for reproduction C is the same as for the reference point for reproduction B; hence in FIG. 7 the identifying symbols of these elements for C are given in parentheses. In FIG. 7 the pulse motors 26 . . . , 27 . . . , 28 . . . and slide mechanisms 23, 24 and 25 are so correlated that the pulse motor 26, for instance, has its drive shaft connected with a precision-threaded screw 29, and a mating nut 30 is provided in one of the slide mechanisms 23 so that the one of the slide mechanisms is caused to slide with respect to the other thereof as the screw 29 rotates. These screws 29 and nuts 30 are all represented by the same symbols (numerals). Numeral 32 designates a base plate.

In this reproducing device 17 indicated by numerals 190, 191 and 192 are holes made from one end the spherical bodies of the spherical joints 20, 21 and 22, provided for setting the face bow 1 on the device 17. Three set screws 6, 18 and 18' of the face bow 1 detached from the patient P are loosened and retaining screws 51, 18 and 18' are rotated 90° so that the tips of the retaining screws 51, 18 and 18' are pointed inward of the face bow 1 as shown in FIG. 1. The tips of the retaining screws 51, 18 and 18' are coaxially inserted into the holes 190, 191 and 192 in the spherical joints 20, 21 and 22 respectively so as to cause the spot light sources A, B and C to agree with the centers of motion of the joints 20, 21 and 22. Even after the above-described rotation, the spot light source A remains on the axis l₃ of the mounting shaft 31, and the spot light sources B and C on the axes l₄ and l₄' of the mounting shafts 71 and 71' so that the positional relationship among these points is identical with that at the time of measurement; hence, when the spot light sources A, B and C are made to agree with the centers of motion of the joints 20, 21 and 22, the reference points for measurement are bound to agree with the reference points for reproduction. When the impression of teeth (not shown) in the impression material on the dental dish 15 fixedly attached to the face bow 1 is copied on or shifted onto the mandibular (lower jaw) model LJ', therefore, the existing position of the dental arch of the patient P is precisely reproduced on this mandibular (lower jaw) model LJ'.

Thus according to the present invention, the patient's dental arch can be precisely reproduced on the mandibular model by simply shifting the face bow used for measurement onto the reproducing device; hence the invention is quite useful when using the above-described diagnostic device. Also, since the reference points are not the auricular holes and the bottom of the orbits (the line linking them), the only requirement is to match the three measuring points with the corresponding reference points for reproduction. The present invention also has the practical advantages of, among others, making the reproducing errors extremely small.

We claim:

1. A face bow for a mandibular motion diagnostic device, said mandibular motion diagnostic device including a mandibular motion measuring device and a reproducing device, said mandibular motion measuring device being arranged such that its relative position with respect to a patient's mandible is kept constant throughout the time of measurement, and measuring the motion of three points set on a rigid plane representing said patient's mandible as the corresponding pieces of position information as a function of time, and said reproducing device being adapted such that there are provided three reference points for reproduction so set that their relative positions with respect to a mandibular model on an articulator are indentical with their relative positions with respect to said patient's mandible and said mandibular model is caused to reproduce the motion of said patient's mandible as motion of said rigid plane defined by said reference points for reproduction according to said position information;

said face bow being characterized in that:
it can extend around a patient's mandible and is set in a fixed positional relationship with said mandibular motion measuring device and is arranged to be shifted onto said mandibular model after the measurement is over and is provided with three spot light sources corresponding with said reference points for measurement which each emit light toward a respective one of said three points on said mandibular motion measuring device, said spot light sources being retained at the tips of retaining screws connected with said face bow and the axes of respective retaining screws are rotatable up to 90° so as to be shiftable from a horizontal plane to be in a vertical plane and a dental dish filled with an impression material connected to be integral therewith so that when said face bow is shifted onto said mandibular model set on said articulator, said spot light sources agree with said reference points for reproduction.

2. A face bow as defined in claim 1, wherein said reference points for measurement comprise one point in the anterior section of said mandible and two points in both lateral sections thereof, said three points defining an isosceles triangle with said one point in said anterior section as a vertex, said reference points corresponding thereto agreeing with the centers of motion of a plurality spherical joints connected with said mandibular model at fixed distances therefrom, and said spot light sources are retained at said centers of motion of said spherical joints.

* * * * *